(12) United States Patent
Dalko et al.

(10) Patent No.: US 7,998,933 B2
(45) Date of Patent: Aug. 16, 2011

(54) PROCESS FOR TREATING THE SKIN COMPRISING APPLYING TO THE SKIN AT LEAST ONE COMPOSITION COMPRISING AT LEAST ONE N-AMINOACYLAMIDE

(75) Inventors: Maria Dalko, Gif sur Yvette (FR); Yann Mahe, Morsang-sur-Orge (FR); Lionel Breton, Versailles (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/843,751

(22) Filed: Jul. 26, 2010

(65) Prior Publication Data

US 2011/0021438 A1    Jan. 27, 2011

Related U.S. Application Data

(60) Continuation of application No. 12/222,147, filed on Aug. 4, 2008, now Pat. No. 7,786,321, which is a continuation of application No. 11/102,812, filed on Apr. 11, 2005, now Pat. No. 7,419,970, which is a division of application No. 10/297,442, filed as application No. PCT/FR01/01559 on May 21, 2001, now Pat. No. 6,987,128.

(30) Foreign Application Priority Data

Jun. 8, 2000 (FR) ..................... 00 07344

(51) Int. Cl.
*A61K 8/64* (2006.01)
*A61Q 19/08* (2006.01)

(52) U.S. Cl. ......... 514/18.8; 514/114; 558/190; 560/41; 562/450

(58) Field of Classification Search .............. 548/163, 548/178

See application file for complete search history.

(56) References Cited

U.S. PATENT DOCUMENTS

| 5,234,909 A | 8/1993 | Philippe |
| 6,987,128 B2 | 1/2006 | Dalko et al. |
| 7,419,970 B2 | 9/2008 | Dalko et al. |

FOREIGN PATENT DOCUMENTS

| EP | 0 498 728 B1 | 8/1992 |
| FR | 1 415 229 | 9/1965 |
| FR | 2810033 A1 | 12/2001 |
| JP | 07-242641 | 9/1995 |
| WO | WO 00/18789 | 4/2000 |
| WO | WO 00/18790 | 4/2000 |
| WO | WO 01/94381 A2 | 12/2001 |

OTHER PUBLICATIONS

Keating et al., Journal of the American Chemical Society, 1996, vol. 118, No. 11, p. 2574-83.*

K. Burger et al., "Incorporation of α-Trifluoromethyl Substituted α-Amino Acids into C-and N-terminal Position of Peptides and Peptide Mimetics Using Multicomponent Reactions," Tetrahedron, vol. 54 (1998), pp. 5915-5928.
Chemische Berichte, vol. 94 (1961), pp. 2802-2814.
Keating et al., Journal of the American Chemical Society, 1996, vol. 118, No. 11, pp. 2574-2583.
M. Waki et al., "Peptide Synthesis Using Four-Component Condensation (Ugi Reaction)," Journal of the Americal Chemical Society, vol. 99, No. 18, Aug. 31, 1997, pp. 6075-6082.
International Search Report for PCT/R01/01559, mailed Jul. 12, 2001.
Interview Summary mailed Jan. 10, 2005, in U.S. Appl. No. 10/297,442 (patented as US 6,987,128).
Office Action mailed Nov. 14, 2003, in U.S. Appl. No. 10/297,442 (patented as US 6,987,128).
Office Action mailed May 10, 2007, in U.S. Appl. No. 11/102,812 (patented as US 7,419,970).
Office Action mailed Dec. 12, 2007, in U.S. Appl. No. 11/102,812 (patented as US 7,419,970).
Zhurnai Obshchei Khimii, vol. 30, No. 4 (1960) pp. 1148-1153—Journal of General Chemistry of the USSR, vol. 30, No. 4 (1960), pp. 1165-1168.
"Zhurnal Obshchei Khimii, vol. 32, No. 9 (1962), pp. 2809-2812"—Journal of General Chemistry of the USSR, vol. 32, No. 9 (1962), pp. 2768-2769.
Dallob, et al. Journal of Clinical Endocrinology and metabolism, 1994, vol. 79, No. 3, pp. 703-706.
Google search results on N-acylamino amide for preventing hair loss. (2007).
English language Derwent abstract of FR 1 415 229. (1966).
English language Derwent abstract of JP 07-242641 (1995).
Interview Summay mailed Jan. 10, 2005 in U.S. Appl. No. 10297,442 (patented as US 6,987,128).
Office Action mailed Nov. 14, 2003, in U.S. Appl. No. 10/297,442 (patented as US 6,987,128).
Office Action mailed May 10, 2007, in U.S. Appl. No. 11/102,812 (patented as US 7,419,970).
Office Action mailed Dec. 12, 2007, in U.S. Appl. No. 11/102,812 (patented as US 7,419,970).
Preliminary STN search_12222146 (2009).
Shkodinskaya et al., Abstract of Voprosy Onkologii (1979), 25 (10), pp. 29-33.
Zhurnai Obshchei Khimii, vol. 30, No. 4 (1960) pp. 1148-1153—Journal of General Chemistry of the USSR, vol. 30, No. 4 (1960), pp. 1165-1168.
"Zhurnal Obshchei Khimii, vol. 32, No. 9 (1962), pp. 2809-2812"—Journal of General Chemistry of the USSR, vol. 32, No. 9 (1962), pp. 2768-2769.

* cited by examiner

*Primary Examiner* — Yong Chu
(74) *Attorney, Agent, or Firm* — Finnegan, Henderson, Farabow, Garrett & Dunner, LLP

(57) ABSTRACT

The invention concerns novel compounds of the N-acylamino-amide family, compositions, in particular cosmetic or pharmaceutical, containing them, and their use for treating body or face skin ageing, whether chronobiologic or light-induced, and in particular skin ageing caused by decrease of skin elasticity and/or by collagen degradation in the structure of tissues.

21 Claims, No Drawings

PROCESS FOR TREATING THE SKIN COMPRISING APPLYING TO THE SKIN AT LEAST ONE COMPOSITION COMPRISING AT LEAST ONE N-AMINOACYLAMIDE

This application is a continuation of application Ser. No. 12/222,147, filed Aug. 4, 2008, now U.S. Pat. No. 7,786,321, which is a continuation of application Ser. No. 11/102,812, filed Apr. 11, 2005, now U.S. Pat. No. 7,419,970 B2, which is a divisional of application Ser. No. 10/297,442, filed Dec. 6, 2002, now issued as U.S. Pat. No. 6,987,128, which is the National Stage of International Application No. PCT/FR01/01559, filed May 21, 2001, claiming priority to French Application No. 00/07344, filed Jun. 8, 2000.

The present invention relates to novel compounds of the N-acylamino amide family, to their use in particular in cosmetics or in pharmaceuticals, and to compositions comprising them.

Human skin consists of two compartments, i.e. a superficial compartment, the epidermis, and a deep compartment, the dermis.

Natural human epidermis is composed mainly of three types of cell: the keratinocytes, which form the vast majority, the melanocytes and the Langerhans cells. Each of these cell types contributes, by virtue of its intrinsic functions, towards the essential role played in the body by the skin.

The dermis gives the epidermis a solid support. It is also the epidermis' nourishing factor. It consists mainly of fibroblasts and of an extracellular matrix itself composed mainly of collagen, elastin and a substance, known as ground substance, these components being synthesized by the fibroblast. Leukocytes, mastocytes and tissue macrophages are also found in the dermis. Finally, the dermis contains blood vessels and nerve fibres.

It is known that during a superficial cutaneous stress, which may in particular be of chemical, physical or bacterial origin, the keratinocytes of the superficial layers of the epidermis release biological mediators which have the ability to attract certain cells which infiltrate the skin, which are themselves responsible for maintaining transient local irritation.

Among the biological mediators which may be produced by the keratinocytes thus stressed, mention may be made of chemokines, which are chemoattractant cytokines that are responsible for recruiting leukocytes to the sites of inflammation, including interleukin 8 (IL-8) which is more particularly responsible for recruiting neutrophils.

These cells infiltrating the irritated or attacked areas then release enzymes, among which mention may be made of leukocyte elastase.

Due in particular to the action of this enzyme, the extracellular supporting elastic fibres of the connective tissue may be degraded, and thus result in a reduction in the elasticity of the skin.

It is even furthermore known that, in synergy with cathepsin G, leukocyte elastase may dissociate the integrity of the epidermis by widening the inter-keratinocyte intercellular spaces.

Thus, in the long-term, the sum of the superficial cutaneous micro-stresses, for example generated by a prolonged exposure to UV or by irritant agents, may result in a more or less accelerated loss of the skin's natural elasticity. The network formed by the elastic fibres of the underlying connective tissue and of the extracellular spaces may then be gradually destructured. This results in accelerated ageing of the skin (wrinkled and/or less supple skin) via the impairment of the dermal elastic network, and also an accentuation of the wrinkles (deeper wrinkles).

Moreover, it is known that the firmness of the dermis is mainly ensured by the collagen fibres. These fibres consist of fibrils sealed together, thus forming more than ten different types of structure. The firmness of the dermis is largely due to the overlapping of the collagen fibres packed together in all directions. The collagen fibres play a part in the elasticity and tonicity of the skin and/or the mucous membranes.

The collagen fibres are constantly being renewed, but this renewal diminishes with age, resulting in a thinning of the dermis. This thinning of the dermis is also due to pathological causes such as, for example, the hypersecretion of corticoid hormones, certain pathologies or vitamin deficiencies (in the case of vitamin C in scurvy). It is also accepted that extrinsic factors such as ultraviolet rays, tobacco or certain treatments (glucocorticoids, vitamin D and derivatives, for example) also have an effect on the skin and on its collagen content.

Although very strong, collagen fibres are sensitive to certain enzymes known as collagenases. A degradation of the collagen fibres results in the appearance of flaccid and wrinkled skin, which people, preferring the appearance of smooth and taut skin, have always endeavoured to combat.

Moreover, at the menopause, the main changes regarding the dermis are a decrease in the collagen content and in the thickness of the dermis. In menopausal women, this results in a thinning of the skin and/or of the mucous membranes. Women then experience a "dry skin" sensation or a sensation of skin under tension, and an accentuation of the surface lines and fine wrinkles is observed. The skin has a coarse appearance when touched. Finally, the suppleness of the skin is reduced.

One aim of the present invention is to propose a solution to these various problems, and in particular to propose novel compounds which may be used in cosmetics or in pharmaceuticals to limit the ageing of the skin, whether chronobiological or light-induced ageing, and in particular the ageing generated by a reduction in the elasticity of the skin and/or by a degradation of the collagen in the structure of the tissues.

Without being bound by the present explanation, it may be considered that the fact of providing, to the keratinocytes of the surface layers of the skin, compounds capable of slowing down the degradation activity of the elastic fibres of the intercellular spaces, may make it possible to reduce this phenomenon of accelerated ageing of the skin, due to superficial cutaneous stresses.

Certain compounds belonging to the family of N-acylamino amides are known in the prior art. Examples that may be mentioned include the document *J. Am. Chem. Soc.,* 1977, 99(18), pp. 6075-82) which describes a process for synthesizing the following derivatives:

N-acetylglycyl-N-(benzyl)-DL-valylglycine tert-butyl ester;
N-acetylglycyl-N-(2-nitrobenzyl)-DL-valylglycine tert-butyl ester;
N-acetylglycyl-N-(2,4-dimethyloxybenzyl)-DL-valylglycine tert-butyl ester.

One subject of the present invention is thus a compound of formula (I) as defined below, with the exception of the following derivatives:

N-acetylglycyl-N-(benzyl)-DL-valylglycine tert-butyl ester;
N-acetylglycyl-N-(2-nitrobenzyl)-DL-valylglycine tert-butyl ester;
N-acetylglycyl-N-(2,4-dimethyloxybenzyl)-DL-valylglycine tert-butyl ester.

A subject of the invention is also a composition comprising, in a physiologically acceptable medium, at least one such compound of formula (I).

Another subject of the invention is the use of at least one compound of formula (I), or of a composition comprising it, to treat, preventively or curatively, the signs of ageing of facial or body skin, whether chronobiological or light-induced ageing, and in particular the ageing generated by a reduction in the elasticity of the skin and/or by a degradation of the collagen in the structure of the tissues.

Another subject of the invention is the use of at least one compound of formula (I), or of a composition comprising it, to treat, preventively or curatively, wrinkles and/or fine lines, wizened skin, a lack of elasticity and/or of tonus of the skin, thinning of the dermis, the degradation of collagen fibres, flaccid skin and thinned skin; the internal degradation of the skin following exposure to ultraviolet radiation.

Another subject of the invention is the use of at least one compound of formula (I), or of a composition comprising it, to inhibit the activity of elastases and/or to limit and/or combat the degradation of the elastic fibres.

Another subject of the invention is a cosmetic treatment process for facial or body skin, including the scalp, in which a cosmetic composition as defined below is applied to the skin.

Specifically, it has been found that the compounds of formula (I) have inhibitory activity on the activity of elastases, and that they may thus be used to limit and/or combat the degradation of the elastic fibres.

It follows therefrom that they may be used in or for the preparation of a composition, the compounds or the composition being intended to treat, preventively and/or curatively, the signs of ageing of the skin.

The expression "signs of ageing of the skin" means any changes in the outer appearance of the skin that are due to ageing, whether chronobiological and/or light-induced ageing, such as, for example, wrinkles and fine lines, wizened skin, a lack of elasticity and/or of tonus of the skin, thinning of the dermis and/or degradation of the collagen fibres which results in the appearance of flaccid and wrinkled skin; it is also understood to mean any internal changes in the skin which are not automatically reflected by a changed outer appearance, such as, for example, all internal degradations of the skin, particularly of the elastin fibres, or elastic fibres, following exposure to ultraviolet radiation.

One advantage of the present invention lies in the fact that the compounds of formula (I) may be readily prepared.

The compounds which may be used in the present invention thus correspond to formula (I) below:

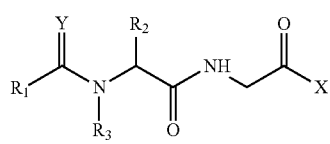

(I)

in which:
the radical Y represents O or S,
the radical R1 represents:
(i) a hydrogen atom;
(ii) a linear, branched or cyclic, saturated or unsaturated hydrocarbon-based radical containing 1 to 18 carbon atoms,
optionally substituted with 1 to 5 groups, which may be identical or different, chosen from —OH; —OR; —O—COR; —SH; —SR; —S—COR; —NH$_2$; —NHR; —NRR'; —NH—COR; -Hal (halogen); —CN; —COOR; —COR; —P(O)—(OR)$_2$; —SO$_2$—OR; with R and R' representing, independently of each other, a linear, branched or cyclic, saturated or unsaturated hydrocarbon-based radical containing 1 to 6 carbon atoms, which is optionally halogenated, or even perhalogenated,
the said radicals R and R' possibly forming together with N a 5- or 6-membered carbon-based ring which may also comprise at least one hetero atom chosen from O, N and/or S in the ring, and/or which may be substituted with 1 to 5 groups, which may be identical or different, chosen from —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon-based radical containing 1 to 6 carbon atoms, which is optionally halogenated, or even perhalogenated;

(iii) a radical chosen from the following radicals: —OR; —NH$_2$; —NHR; —NRR'; —NH—COR; —COOR; —COR; with R and R' representing, independently of each other, a linear, branched or cyclic, saturated or unsaturated hydrocarbon-based radical containing 1 to 6 carbon atoms, which is optionally halogenated, or even perhalogenated, the said radicals R and R' possibly forming together with N a 5- or 6-membered carbon-based ring which may also comprise at least one hetero atom chosen from O, N and/or S in the ring, and/or which may be substituted with 1 to 5 groups, which may be identical or different, chosen from —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon-based radical containing 1 to 6 carbon atoms, which is optionally halogenated, or even perhalogenated;

the radical R2 represents a linear, branched or cyclic, saturated or unsaturated hydrocarbon-based radical containing 1 to 18 carbon atoms, optionally substituted with 1 to 5 groups, which may be identical or different, chosen from —OH; —OR; —O—COR; —SH; —SR; —S—COR; —NH$_2$; —NHR; —NRR'; —NH—COR; -Hal (halogen); —CN; —COOR; —COR;
with R and R' representing, independently of each other, a linear, branched or cyclic, saturated or unsaturated hydrocarbon-based radical containing 1 to 6 carbon atoms, which is optionally halogenated, or even perhalogenated,
the said radicals R and R' possibly forming together with N a 5- or 6-membered carbon-based ring which may also comprise at least one hetero atom chosen from O, N and/or S in the ring, and/or which may be substituted with 1 to 5 groups, which may be identical or different, chosen from —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon-based radical containing 1 to 6 carbon atoms, which is optionally halogenated, or even perhalogenated;

the radical R3 represents a radical chosen from those of formula (II) or (III):

(II)

(III)

in which:
y is an integer between 0 and 5 inclusive and y' is an integer between 1 and 5 inclusive;
A is a linear or branched, saturated or unsaturated divalent hydrocarbon-based radical containing 1 to 18 carbon atoms, optionally substituted with 1 to 5 groups, which may be identical or different, chosen from —OH; —OR;

—O—COR; —SH; —SR; —S—COR; —NH$_2$; —NHR; —NRR'; —NH—COR; -Hal (halogen, or even perhalogen); —CN; —COOR; —COR; —NO$_2$; —SO$_2$—OR;

with R and R' representing, independently of each other, a linear, branched or cyclic, saturated or unsaturated hydrocarbon-based radical containing 1 to 6 carbon atoms, which is optionally halogenated, or even perhalogenated, the said radicals R and R' possibly forming together with N a 5- or 6-membered carbon-based ring which may also comprise at least one hetero atom chosen from O, N and/or S in the ring, and/or which may be substituted with 1 to 5 groups, which may be identical or different, chosen from —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon-based radical containing 1 to 6 carbon atoms, which is optionally halogenated, or even perhalogenated;

B represents at least one group, which may be identical or different, chosen from —OH; —OR; —O—COR; —SH; —SR; —S—COR; —NH$_2$; —NHR; —NRR'; —NH—COR; -Halogen; —CN; —COOR; —COR; —NO$_2$; —SO$_2$—OR, or represents a linear or branched, saturated or unsaturated hydrocarbon-based radical containing 1 to 18 carbon atoms, optionally substituted with 1 to 5 groups, which may be identical or different, chosen from —OH; —OR; —O—COR; —SH; —SR; —S—COR; —NH$_2$; —NHR; —NRR'; —NH—COR; -Hal (halogen, or even perhalogen); —CN; —COOR; —COR; —NO$_2$; —SO$_2$—OR;

with R and R' representing, independently of each other, a linear, branched or cyclic, saturated or unsaturated hydrocarbon-based radical containing 1 to 6 carbon atoms, which is optionally halogenated, or even perhalogenated, the said radicals R and R' possibly forming together with N a 5- or 6-membered carbon-based ring which may also comprise at least one hetero atom chosen from O, N and/or S in the ring, and/or which may be substituted with 1 to 5 groups, which may be identical or different, chosen from —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon-based radical containing 1 to 6 carbon atoms, which is optionally halogenated, or even perhalogenated;

the radical X represents a radical chosen from —OH, —OR$_4$, —NH$_2$, —NHR$_4$, —NR$_4$R$_5$, —SR$_4$, —COOR$_4$ and —COR$_4$; with R$_4$ and R$_5$ representing, independently of each other, a linear, branched or cyclic, saturated or unsaturated hydrocarbon-based radical containing 1 to 6 carbon atoms, optionally substituted with 1 to 5 groups, which may be identical or different, chosen from —OH; —OR; —O—COR; —SH; —SR; —S—COR; —NH$_2$; —NHR; —NRR'; —NH—COR; -Hal (halogen, or even perhalogen); —CN; —COOR; —COR; with R and R' representing, independently of each other, a linear, branched or cyclic, saturated or unsaturated hydrocarbon-based radical containing 1 to 6 carbon atoms, which is optionally halogenated, or even perhalogenated, the said radicals R and R' possibly forming together with N a 5- or 6-membered carbon-based ring which may also comprise at least one hetero atom chosen from O, N and/or S in the ring, and/or which may be substituted with 1 to 5 groups, which may be identical or different, chosen from —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon-based radical containing 1 to 6 carbon atoms, which is optionally halogenated, or even perhalogenated;

the said radicals R$_4$ and R$_5$ possibly forming together with N a 5- or 6-membered carbon-based ring which may also comprise at least one hetero atom chosen from O, N and/or S in the ring, and/or which may be substituted with 1 to 5 groups, which may be identical or different, chosen from —OH; —OR"; —O—COR"; —SH; —SR"; —S—COR"; —NH$_2$; —NHR"; —NH—COR"; -Hal (halogen); —CN; —COOR"; —COR"; with R" representing a linear, branched or cyclic, saturated or unsaturated hydrocarbon-based radical containing 1 to 6 carbon atoms, which is optionally halogenated, or even perhalogenated, with the exception of the following derivatives:
N-acetylglycyl-N-(benzyl)-DL-valylglycine tert-butyl ester;
N-acetylglycyl-N-(2-nitrobenzyl)-DL-valylglycine tert-butyl ester;
N-acetylglycyl-N-(2,4-dimethyloxybenzyl)-DL-valylglycine tert-butyl ester.

Also included in this definition are the mineral acid or organic acid salts of the said compounds, and also the optical isomers thereof, in isolated form or as a racemic mixture.

The expression "linear, branched or cyclic hydrocarbon-based radical" in particular means radicals of alkyl, aryl, aralkyl, alkylaryl, alkenyl or alkynyl type.

The C$_6$H$_5$ group present in the radical R3 should be understood as being a cyclic aromatic group.

The radical Y preferably represents oxygen.

Preferably, the radical R1 represents hydrogen or a linear or branched, saturated or unsaturated, optionally substituted hydrocarbon-based radical containing 1 to 12 and in particular 1, 2, 3, 4, 5 or 6 carbon atoms.

In particular, the substituents may be chosen from —OH, —OR and/or —P(O)—(OR)$_2$ with R representing a linear, branched or cyclic, saturated or unsaturated hydrocarbon-based radical containing 1 to 6 carbon atoms, which is optionally halogenated, or even perhalogenated.

The radical R1 preferably represents a methyl, ethyl, propyl or isopropyl radical, optionally substituted with a group —OH or —P(O)—(OR)$_2$ with R representing methyl, ethyl, propyl or isopropyl.

Preferably, the radical R2 represents a linear, branched or cyclic, saturated or unsaturated, optionally substituted hydrocarbon-based radical containing 1 to 12 and in particular 1, 2, 3, 4, 5 or 6 carbon atoms.

In particular, the substituents may be chosen from —OH and —OR with R representing a linear, branched or cyclic, saturated or unsaturated hydrocarbon-based radical containing 1 to 6 carbon atoms, which is optionally halogenated, or even perhalogenated.

The radical R2 preferably represents a methyl, ethyl, propyl, isopropyl, n-butyl, tert-butyl or isobutyl radical.

The radical R3 preferably represents a radical of formula —C$_6$H$_{(5-y')}$—B$_{y'}$ for which y'=1, 2 or 3; or a radical of formula -A-C$_6$H$_{(5-y)}$—B$_y$ for which y=0, 1 or 2. Preferably, A is a linear or branched, saturated or unsaturated, optionally substituted divalent hydrocarbon-based radical containing 1 to 12 carbon atoms.

The substituents of A are preferably chosen from -Hal (halogen, or even perhalogen); —CN; —COOR; —NO$_2$; —SO$_2$—OR; with R representing a linear, branched or cyclic, saturated or unsaturated hydrocarbon-based radical containing 1 to 6 carbon atoms, which is optionally halogenated, or even perhalogenated.

Preferably, B represents at least one group —OR; —NHR; —CN; —COOR; —COR or represents a hydrocarbon-based radical chosen from a linear or branched, saturated or unsaturated, optionally substituted hydrocarbon-based radical containing 1 to 12 carbon atoms.

The substituents of B are preferably chosen from -Hal (halogen, or even perhalogen); —CN; —COOR; —NO₂; —SO₂—OR; with R representing a linear, branched or cyclic, saturated or unsaturated hydrocarbon-based radical containing 1 to 6 carbon atoms, which is optionally halogenated, or even perhalogenated.

The radical R3 preferably represents a group chosen from one of the following formulae:

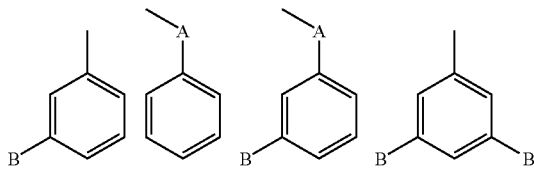

in which A and B have the above meanings.

In particular, the divalent radical A may be a methylene, an ethylene or a propylene.

Preferably, the radical B represents at least one group —OR; —NHR; —CN; COOR; —COR for which R denotes a methyl, ethyl, propyl or isopropyl radical or represents a hydrocarbon-based radical chosen from a methyl, ethyl, propyl or isopropyl radical, substituted with one or more halogens, in particular chlorine, bromine, iodine or fluorine, and preferably totally halogenated (perhalogenated), such as perfluorinated. Mention may be made in particular of the perfluoromethyl radical (—CF₃) as being most particularly preferred.

Preferably, the radical X represents a radical chosen from —OH and —OR₄ with R₄ representing a linear, cyclic or branched, saturated or unsaturated hydrocarbon-based radical containing 1 to 6 carbon atoms, which is optionally substituted.

The substituents may be chosen from —OH and —OR with R representing a linear, branched or cyclic, saturated or unsaturated hydrocarbon-based radical containing 1 to 6 carbon atoms, which is optionally halogenated, or even perhalogenated.

Preferably, the radical X represents a radical chosen from —OH, —OCH₃, —OC₂H₅, —O—C₃H₇ and —OC₄H₉.

Among the compounds that are particularly preferred, mention may be made of:
{2-[acetyl(3-trifluoromethylphenyl)amino]-3-methylbutyrylamino}acetic acid,
ethyl {2-[acetyl(3-trifluoromethylphenyl)amino]-3-methylbutyrylamino}acetate,
[2-(acetylbenzylamino)-3-methylbutyrylamino]acetic acid,
ethyl[2-(acetylbenzylamino)-3-methylbutyrylamino]-acetate,
ethyl (2-{benzyl[(diethoxyphosphoryl)acetyl]amino}-3-methylbutyrylamino)acetate.

The compounds according to the invention may be readily prepared by a person skilled in the art on the basis of his general knowledge. In particular, a carboxylic acid, an aldehyde, an amine compound and an isonitrile may be reacted together in an Ugi reaction.

Needless to say, during the synthesis of the compounds according to the invention, and depending on the nature of the various radicals present on the starting compounds, a person skilled in the art may take care to protect certain substituents so that they do not participate in the rest of the reactions.

The amount of compound to be used in the compositions according to the invention may be readily determined by a person skilled in the art, as a function of the nature of the compound used, the individual to be treated and/or the desired effect. In general, this amount may be between 0.00001% and 20% by weight relative to the total weight of the composition, in particular between 0.001% and 10% by weight, preferably between 0.05% and 5% by weight, better still between 0.1% and 2% by weight and preferentially between 0.5% and 1% by weight.

The compounds of formula (I) may be used in particular, alone or as a mixture, in a composition which comprises a physiologically acceptable medium, in particular in a cosmetic or pharmaceutical composition which thus moreover comprises a cosmetically or pharmaceutically acceptable medium.

The physiologically acceptable medium in which the compounds according to the invention may be used, and the constituents thereof, the amount thereof, the presentation form of the composition and its method of preparation, may be chosen by a person skilled in the art on the basis of his general knowledge depending on the type of composition desired.

In general, this medium may be anhydrous or aqueous. It may thus comprise an aqueous phase and/or a fatty phase.

For an application to the skin, the composition may be in particular in the form of an aqueous or oily solution; a dispersion of the lotion or serum type; emulsions of liquid or semi-liquid consistency of the milk type obtained by dispersing a fatty phase in an aqueous phase (O/W emulsion) or, conversely (W/O emulsion); suspensions or emulsions of soft consistency of the aqueous or anhydrous gel or cream type; microcapsules or microparticles; vesicular dispersions of ionic and/or nonionic type.

For an application on the hair, the composition may be in the form of aqueous, alcoholic or aqueous-alcoholic solutions; in the form of creams, gels, emulsions or mousses; in the form of aerosol compositions also comprising a propellant under pressure.

When the composition is in aqueous form, in particular in the form of an aqueous dispersion, emulsion or solution, it may comprise an aqueous phase, which may comprise water, a floral water and/or a mineral water.

The said aqueous phase may also comprise alcohols such as C₁-C₆ monoalcohols and/or polyols such as glycerol, butylene glycol, isoprene glycol, propylene glycol or polyethylene glycol.

When the composition according to the invention is in the form of an emulsion, it may optionally also comprise a surfactant, preferably in an amount of from 0.01% to 30% by weight relative to the total weight of the composition. The composition according to the invention may also comprise at least one coemulsifier which may be chosen from oxyethylenated sorbitan monostearate, fatty alcohols such as stearyl alcohol or cetyl alcohol, or fatty acid esters of polyols, such as glyceryl stearate.

The composition according to the invention may also comprise a fatty phase consisting in particular of fatty substances that are liquid at 25° C., such as volatile or non-volatile oils of animal, plant, mineral or synthetic origin; fatty substances that are solid at 25° C., such as waxes of animal, plant, mineral or synthetic origin; pasty fatty substances; gums; mixtures thereof.

The volatile oils are generally oils having, at 25° C., a saturating vapour pressure at least equal to 0.5 millibar (i.e. 50 Pa).

Among the constituents of the fatty phase which may be mentioned are:

cyclic volatile silicones containing from 3 to 8 and preferably from 4 to 6 silicon atoms, cyclocopolymers such as dimethylsiloxane/methylalkylsiloxane, linear volatile silicones containing from 2 to 9 silicon atoms, volatile hydrocarbon-based oils, such as isoparaffins and in particular isododecane and fluoro oils, poly($C_1$-$C_{20}$) alkylsiloxanes and in particular those containing trimethylsilyl end groups, among which mention may be made of linear polydimethylsiloxanes and alkylmethylpolysiloxanes such as cetyldimethicone (CTFA name), silicones modified with aliphatic and/or aromatic groups, which may contain fluorine, or with functional groups such as hydroxyl, thiol and/or amine groups, phenylsilicone oils, oils of animal, plant or mineral origin, and in particular animal or plant oils formed by fatty acid esters of polyols, in particular liquid triglycerides, for example sunflower oil, corn oil, soybean oil, marrow oil, grape seed oil, sesame oil, hazelnut oil, apricot oil, almond oil or avocado oil; fish oils, glyceryl tricaprocaprylate, or plant or animal oils of formula $R_1COOR_2$ in which $R_1$ represents a higher fatty acid residue containing from 7 to 19 carbon atoms and $R_2$ represents a branched hydrocarbon-based chain containing from 3 to 20 carbon atoms, for example purcellin oil; liquid paraffin, liquid petroleum jelly, perhydrosqualene, wheatgerm oil, beautyleaf oil, sesame oil, macadamia oil, grape seed oil, rapeseed oil, coconut oil, groundnut oil, palm oil, castor oil, jojoba oil, olive oil or cereal germ oil; fatty acid esters; alcohols; acetylglycerides; alkyl or polyalkyl octanoates, decanoates or ricinoleates; fatty acid triglycerides; glycerides;

fluoro oils and perfluoro oils;

silicone gums, waxes of animal, plant, mineral or synthetic origin, such as microcrystalline waxes, paraffin, petrolatum, petroleum jelly, ozokerite, montan wax; beeswax, lanolin and its derivatives; candelilla wax, ouricury wax, carnauba wax, Japan wax, cocoa butter, cork fibre wax or sugar cane wax; hydrogenated oils that are solid at 25° C., ozokerites, fatty esters and glycerides that are solid at 25° C.; polyethylene waxes and waxes obtained by Fischer-Tropsch synthesis; hydrogenated oils that are solid at 25° C.; lanolins; fatty esters that are solid at 25° C.; silicone waxes; fluoro waxes.

In a known manner, the composition according to the invention may comprise adjuvants that are common in the field under consideration, such as hydrophilic or lipophilic gelling agents, hydrophilic or lipophilic additives, hydrophilic or lipophilic active agents, in particular cosmetic or pharmaceutical active agents, preserving agents, antioxidants, solvents, fragrances, fillers, pigments, nacres, UV screening agents, odour absorbers and colorants. Depending on their nature, these adjuvants may be introduced into the fatty phase, into the aqueous phase and/or into lipid spherules.

The nature and amount of these adjuvants may be chosen by a person skilled in the art, on the basis of his general knowledge, so as to obtain the desired presentation form for the composition. In any case, a person skilled in the art will take care to select all the optional additional compounds and/or the amount thereof, such that the advantageous properties of the composition according to invention are not, or are not substantially, adversely affected by the addition envisaged.

The cosmetic or pharmaceutical compositions according to the invention may be in particular in the form of a composition intended to care for and/or treat ulcerated areas or areas which have suffered cutaneous stress or microstress, brought about in particular by exposure to UV and/or by coming into contact with an irritant product.

Thus, the compositions according to the invention may be in particular in the form:

of a care, treatment, cleansing or protective product for facial or body skin, including the scalp, such as a care composition (moisturizing day or night composition) for the face or the body; an anti-wrinkle or anti-ageing composition for the face; a matt-effect composition for the face; a composition for irritated skin; a make-up-removing composition; a body milk, in particular a moisturizing and optionally after-sun body milk;

of an anti-sun composition, an artificial tanning (self-tanning) composition or an after-sun care composition;

of a haircare composition, and in particular an anti-sun cream or gel; a scalp care composition, in particular to prevent hair loss or to promote regrowth of the hair; an anti-parasite shampoo;

of a make-up product for the skin of the face, the body or the lips, such as a foundation, a tinted cream, a blusher, an eye shadow, a free or compact powder, a concealer stick, a cover stick, a lipstick or a lipcare product;

of an oral hygiene product such as a toothpaste or an oral rinsing lotion.

The compositions according to the invention find a preferred application as a facial skincare composition, of anti-wrinkle or anti-ageing type, and as an anti-sun or after-sun composition.

A subject of the present invention is also a cosmetic treatment process for facial or body skin, including the scalp, in which a cosmetic composition comprising an effective amount of at least one compound of formula (I) is applied to the skin, left in contact with the skin and then optionally rinsed off.

The cosmetic treatment process of the invention may be carried out in particular by applying the cosmetic compositions as defined above, according to the usual technique for using these compositions. For example: application of creams, gels, sera, lotions, make-up-removing milks or anti-sun compositions to the skin or to dry hair; application of a scalp lotion to wet hair; application of toothpaste to the gums;

The invention is illustrated in further detail in the examples which follow.

EXAMPLE 1

Preparation of ethyl (2-[acetyl(3-trifluoromethylphenyl)amino]-3-methylbutyrylamino)acetate of Formula 0.63 ml of isobutyraldehyde and 1 ml of trifluoromethylamine (1.15 eq) are mixed together in 15 ml of methanol, with stirring. The mixture is left to react for 15 minutes at 20° C., 0.46 ml of acetic acid (1.15 eq) is then added and the mixture is left to react for 10 minutes at 20° C. 0.8 ml of 95% ethyl isocyanoacetate (1 eq) is then added and the mixture is left to react for 48 hours at 20° C.

The reaction medium is concentrated on a rotovapor and the residue is purified on a column of silica (eluent: 3/7 heptane/ethyl acetate: Rf=0.5).

2.45 g of compound are obtained in the form of a waxy solid, equivalent to a yield of 91%.

$^1$H NMR (200 MHz; CDCl$_3$) δ ppm: 0.9 (6H; q), 1.3 (3H; t), 1.8 (3H; s), 2.3 (1H; m), 4.0 (2H, q), 4.2 (2H; q), 4.4 (2H; d), 7.3 (1H; t), 7.5 (4H; m)

EXAMPLE 2

Preparation of {2-[acetyl (3-trifluoromethylphenyl)amino]-3-methylbutyrylamino}acetic acid of Formula

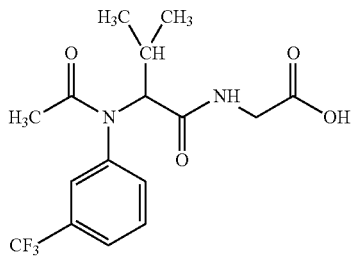

2 g of compound prepared in Example 1 are dissolved in 30 ml of acetone. 30 ml of 2N sodium hydroxide are added and the mixture is left to react for 6 hours at 20° C. The reaction medium is concentrated on a rotovapor. The residual aqueous phase is acidified to pH 2 by adding concentrated HCl and the resulting mixture is then extracted with CH$_2$Cl$_2$.

The organic phase is concentrated to dryness after drying over sodium sulphate. A residue is obtained, which is dissolved with an aqueous 10% basic ethanol mixture and is then reacidified to pH 2 with concentrated HCl. It is re-extracted with CH$_2$Cl$_2$ and the organic phase is dried over sodium sulphate, filtered and concentrated to dryness under vacuum on a rotovapor.

1.3 g of compound are obtained in the form of a slightly light brown solid, equivalent to a yield of 70%.

$^1$H NMR (200 MHz; DMSO) δ ppm: 0.9 (6H; q), 3.7 (2H; m), 1.8 (4H; m), 4.8 (2H; d), 7.6 (4H, m), 8.4 (1H; t), 12.5 (1H; s)

EXAMPLE 3

The in vitro anti-elastase activity of compounds according to the invention with respect to human leukocyte elastase (HLE) was determined.

The test is carried out in the following way: A substrate Me-OSAAPV-p-NA (methyl-O-succinate alanine alanine proline valine-p-nitroanilide) on which is applied HLE (40 milliunits per ml) and 0.1% of the test compound is incubated at 37° C. for 60 minutes.

The percentage inhibition of the control elastase activity is then determined by spectrophotometry.

The test compounds are as follows:
Compound A: {2-[acetyl(3-trifluoromethylphenyl)amino]-3-methylbutyrylamino}acetic acid Compound B: ethyl [2-{benzyl((diethoxyphosphoryl)acetyl]amino}-3-methylbutyrylamino)acetate
Compound C: [2-(acetylbenzylamino)-3-methylbutyrylamino]acetic acid
Compound D: ethyl [2-(acetylbenzylamino)-3-methylbutyrylamino]acetate The following results are obtained:

| Compound (concentration: 0.1%) | % inhibition of the control elastase activity |
|---|---|
| Compound A | 67% |
| Compound B | 17% |
| Compound C | 20% |
| Compound D | 13% |

The percentage inhibition of the control elastase activity is determined in the same way for compound A, at different concentrations.

The following results are obtained:

| Concentration of compound A | % inhibition of the control elastase activity |
|---|---|
| 0.01% | 53% |
| 0.05% | 50% |
| 0.1% | 68% |
| 0.2% | 68% |

Compound A thus induces a strong inhibition of the elastase activity, even in a small amount.

EXAMPLE 4

The ex vivo activity of the compound of Example 2 was evaluated on surviving human skin treated with human leukocyte elastase (HLE).

The test is carried out in the following way:

Fresh sections of human skin, obtained from 2 different donors, are treated for 2 hours at 20° C. with 20 µl of buffer solution (pH 7.4) optionally comprising 10 µg/ml of HLE and optionally 0.1% of the test compound, optionally predissolved in ethanol.

The elastic fibres are stained blue with (+)-catechin and morphometrically quantified by computer-assisted image analysis. The percentage of average dermal surface area occupied by the elastic fibres is thus evaluated.

The following results are obtained:

| | % of surface area occupied by the elastic fibres | |
|---|---|---|
| | Skin 1 | Skin 2 |
| Control (untreated skin) | 12.7% | 15.25% |
| Skin treated with HLE | 4.85% | 6.85% |
| Skin treated with HLE + compound of Example 2 | 13.95% | 11.85% |

It is thus found that the compound according to the invention generates a significant protection of the skins with respect to the destruction of the elastic fibres which is induced by elastase.

EXAMPLE 5

The ex vivo activity of the compound of Example 2 was evaluated on surviving human skin treated with human leukocyte elastase (HLE).

The test is carried out in the following way:

Fragments of normal human skin obtained from three different donors are placed in inserts positioned in culture wells. Culture medium supplemented with antibiotics is placed in the bottom of the wells. A passage is carried out by slow diffusion between the two compartments by means of a porous membrane (pore size: 12 µm).

The culture medium is freshened every three days.

0.5 µg of HLE per ml of culture medium is optionally added to the skin fragments.

5 µl of the test compound, predissolved at a concentration of 0.2% by weight in ethanol, is also added every two days.

The skins are kept alive for 10 days at 37° C.

The elastic fibres are stained blue with (+)-catechin and morphometrically quantified by computer-assisted image analysis. The percentage of average dermal surface area occupied by the elastic fibres is thus evaluated.

The following results are obtained:

|  | % of surface area occupied by the elastic fibres |
| --- | --- |
| Control (untreated skin) | 7.4% |
| Skin treated with HLE | 5.1% |
| Skin treated with HLE + compound of Example 2 | 7.1% |

It is thus found that the compound according to the invention generates a significant protection of the skins with respect to the destruction of the elastic fibres which is induced by elastase.

EXAMPLE 6

The activity of the compound of Example 2 on surviving human skin irradiated with UVA (8 J/cm$^2$) was evaluated.

The test is carried out in the following way:

Fragments of normal human skin obtained from four different donors are placed in inserts positioned in culture wells. Culture medium supplemented with antibiotics is placed in the bottom of the wells. A passage is carried out by slow diffusion between the two compartments by means of a porous membrane (pore size: 12 µm).

The culture medium is freshened every three days.

5 µl of the test compound, predissolved at a concentration of 0.2% in ethanol, is added to the skin fragments every two days.

The skins are kept alive for 7 days at 37° C.

The skins are irradiated once at 8 J/cm$^2$ (Vilbert-Lourmat RMX-3W lamp).

The elastic fibres are stained blue with (+)-catechin and morphometrically quantified by computer-assisted image analysis. The percentage of average dermal surface area occupied by the elastic fibres is thus evaluated.

The following results are obtained:

|  | Morphometric analysis of the elastic fibres (superficial dermis) | Morphometric analysis of the collagen (superficial dermis) |
| --- | --- | --- |
| Untreated skin | 6.75% | 87% |
| Skin treated with UVA (8 J/cm$^2$) | 3.9% | 81% |
| Skin treated with UVA (8 J/cm$^2$) + compound | 6.8% | 92% |

It is found that the compound according to the invention does indeed have activity with respect to the degradation of elastic fibres in the superficial dermis of skin irradiated with UVA.

This compound also has an adequate effect on protecting collagen.

EXAMPLE 7

Composition for Topical Application

The emulsion below is prepared in a conventional manner (% by weight):

| Compound of Example 1 | 1% |
| --- | --- |
| Propylene glycol isostearate | 13% |
| Polyethylene glycol (8 EO) | 5% |
| Propylene glycol | 3% |
| Pentylene glycol | 3% |
| Glyceryl stearate and polyethylene glycol stearate (100 EO) | 5% |
| Oxyethylenated sorbitan monostearate (20 EO) | 0.5% |
| Oxyethylenated (20 EO) oxypropylenated (5 PO) cetyl alcohol | 1% |
| Gelling agents | 0.5% |
| $C_{12}$-$C_{15}$ alkyl benzoates | 4% |
| Ethanol | 3% |
| Sodium hydroxide | 0.12% |
| Preserving agents | qs |
| Water | qs 100% |

EXAMPLE 8

Facial Care Cream

The oil-in-water emulsion below is prepared in a conventional manner (% by weight):

| Compound of Example 2 | 1% |
| --- | --- |
| Glyceryl stearate | 2% |
| Polysorbate 60 (Tween 60 ® sold by the company ICI) | 1% |
| Stearic acid | 1.4% |
| Triethanolamine | 0.7% |
| Carbomer | 0.4% |
| Liquid fraction of karite butter | 12% |

-continued

| | |
|---|---|
| Perhydrosqualene | 12% |
| Antioxidant | qs |
| Fragrance | qs |
| Preserving agent | qs |
| Water | qs 100% |

EXAMPLE 9

Facial Milk

The milk below is prepared in a conventional manner (% by weight):

| | |
|---|---|
| Liquid petroleum jelly | 7% |
| Compound of Example 2 | 1% |
| Glyceryl monostearate, polyethylene glycol stearate (100 EO) | 3% |
| Carboxyvinyl polymer | 0.4% |
| Stearyl alcohol | 0.7% |
| Soybean proteins | 3% |
| NaOH | 0.4% |
| Preserving agent | qs |
| Water | qs 100% |

EXAMPLE 10

Hair Lotion

The lotion below is prepared in a conventional manner (% by weight):

| | |
|---|---|
| Compound of Example 1 | 1% |
| Propylene glycol | 23% |
| Ethanol | 55% |
| Water | qs 100% |

This lotion may be applied to the scalp of alopecic individuals, to prevent the effects of UV, before and/or after exposure to the sun.

EXAMPLE 11

Lotion for Preventing Hair Loss

The lotion below is prepared in a conventional manner (% by weight):

| | |
|---|---|
| Compound of Example 2 | 1% |
| Propylene glycol | 23% |
| Ethanol | 55% |
| Aminexil | 1.5% |
| Water | qs 100% |

This lotion for preventing hair loss may be applied to the scalp of alopecic individuals.

The invention claimed is:
1. A cosmetic process for treating skin that has at least one sign of ageing, comprising applying to the skin at least one composition comprising, in a physiologically acceptable medium, at least one compound chosen from compounds of formula (I):

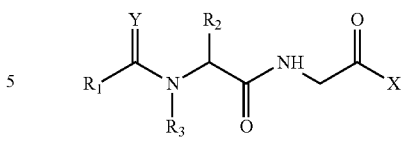

wherein:
Y is chosen from O and S,
$R_1$ is chosen from:
(i) hydrogen;
(ii) linear, branched and cyclic, saturated and unsaturated hydrocarbon-based radicals containing from 1 to 18 carbon atoms,
optionally substituted with 1 to 5 groups, which may be identical or different, chosen from —OH; —OR; —O—COR; —SH; —SR; —S—COR; —NH$_2$; —NHR; —NRR'; —NH—COR; -Hal (halogen); —CN; —COOR; —COR; —P(O)—(OR)$_2$; and —SO$_2$—OR;
wherein R and R', which may be identical or different, are each chosen from linear, branched and cyclic, saturated and unsaturated hydrocarbon-based radicals containing from 1 to 6 carbon atoms, which are optionally substituted with at least one halogen, R and R' optionally forming, together with N in the —NRR', a 5- or 6-membered carbon-based ring which may further comprise at least one hetero atom chosen from O, N and S in the ring, and/or which may be substituted with 1 to 5 groups, which may be identical or different, chosen from —OH; —OR"; —O—COR"; —SH; —SR"; —S—COR"; —NH$_2$; —NHR"; —NH—COR"; -Hal (halogen); —CN; —COOR"; and —COR"; wherein R" is chosen from linear, branched and cyclic, saturated and unsaturated hydrocarbon-based radicals containing from 1 to 6 carbon atoms, which are optionally substituted with at least one halogen; and
(iii) radicals chosen from —OR; —NH$_2$; —NHR; —NRR'; —NH—COR; —COOR; and —COR;
wherein R and R', which may be identical or different, are each chosen from linear, branched and cyclic, saturated and unsaturated hydrocarbon-based radicals containing from 1 to 6 carbon atoms, which are optionally substituted with at least one halogen, R and R' optionally forming, together with N in the —NRR', a 5- or 6-membered carbon-based ring which may further comprise at least one hetero atom chosen from O, N and S in the ring, and/or which may be substituted with 1 to 5 groups, which may be identical or different, chosen from —OH; —OR"; —O—COR"; —SH; —SR"; —S—COR"; —NH$_2$; —NHR"; —NH—COR"; -Hal (halogen); —CN; —COOR"; and —COR"; wherein R" is chosen from linear, branched and cyclic, saturated and unsaturated hydrocarbon-based radicals containing from 1 to 6 carbon atoms, which are optionally substituted with at least one halogen;
$R_2$ is chosen from linear, branched and cyclic, saturated and unsaturated hydrocarbon-based radicals containing from 1 to 18 carbon atoms,
optionally substituted with 1 to 5 groups, which may be identical or different, chosen from —OH; —OR; —O—COR; —SH; —SR; —S—COR; —NH$_2$; —NHR; —NRR'; —NH—COR; -Hal (halogen); —CN; —COOR; and —COR;
wherein R and R', which may be identical or different, are each chosen from linear, branched and cyclic, saturated and unsaturated hydrocarbon-based radicals containing from 1 to 6 carbon atoms, which are optionally substituted with at least one halogen, R and R' optionally forming, together with N in the —NRR', a 5- or 6-membered carbon-based ring which may further comprise at least one hetero atom chosen from O, N and S in the ring, and/or which may be substituted with 1 to 5 groups, which may be identical or different, chosen from —OH; —OR"; —O—COR"; —SH; —SR"; —S—COR"; —NH$_2$; —NHR"; —NH—COR"; -Hal (halogen); —CN; —COOR"; and —COR"; wherein R" is chosen from linear, branched and cyclic, saturated and unsaturated hydrocarbon-based radicals containing from 1 to 6 carbon atoms, which are optionally substituted with at least one halogen;

R$_3$ is a radical chosen from those of formulae (II) and (III):

     (II)

     (III)

wherein:
y is an integer ranging from 0 to 5 and y' is an integer ranging from 1 to 5;
A is chosen from linear and branched, saturated and unsaturated divalent hydrocarbon-based radicals containing from 1 to 18 carbon atoms,
optionally substituted with 1 to 5 groups, which may be identical or different, chosen from —OH; —OR; —O—COR; —SH; —SR; —S—COR; —NH$_2$; —NHR; —NRR'; —NH—COR; -Hal (halogen); —CN; —COOR; —COR; —NO$_2$; and —SO$_2$—OR;
wherein R and R', which may be identical or different, are each chosen from linear, branched and cyclic, saturated and unsaturated hydrocarbon-based radicals containing from 1 to 6 carbon atoms, which are optionally substituted with at least one halogen, R and R' optionally forming, together with N in the —NRR', a 5- or 6-membered carbon-based ring which may further comprise at least one hetero atom chosen from O, N and S in the ring, and/or which may be substituted with 1 to 5 groups, which may be identical or different, chosen from —OH; —OR"; —O—COR"; —SH; —SR";
—S—COR"; —NH$_2$; —NHR"; —NH—COR"; -Hal (halogen); —CN; —COOR"; and —COR"; wherein R" is chosen from linear, branched and cyclic, saturated and unsaturated hydrocarbon-based radicals containing from 1 to 6 carbon atoms, which are optionally substituted with at least one halogen;
B, which may be identical or different, is chosen from —OH; —OR; —O—COR; —SH; —SR; —S—COR; —NH$_2$; —NHR; —NRR'; —NH—COR; -Hal (halogen); —CN; —COOR; —COR; —NO$_2$; and —SO$_2$—OR, and linear and branched, saturated and unsaturated hydrocarbon-based radicals containing from 1 to 18 carbon atoms,
optionally substituted with 1 to 5 groups, which may be identical or different, chosen from —OH; —OR; —O—COR; —SH; —SR; —S—COR; —NH$_2$; —NHR; —NRR'; —NH—COR; -Hal (halogen, or even perhalogen); —CN; —COOR; —COR; —NO$_2$; and —SO$_2$—OR;
wherein R and R', which may be identical or different, are each chosen from linear, branched and cyclic, saturated and unsaturated hydrocarbon-based radicals containing from 1 to 6 carbon atoms, which are optionally substituted with at least one halogen, R and R' optionally forming, together with N in the —NRR', a 5- or 6-membered carbon-based ring which may further comprise at least one hetero atom chosen from O, N and S in the ring, and/or which may be substituted with 1 to 5 groups, which may be identical or different, chosen from —OH; —OR"; —O—COR"; —SH; —SR";
—S—COR"; —NH$_2$; —NHR"; —NH—COR"; -Hal (halogen); —CN; —COOR"; and —COR"; wherein R" is chosen from linear, branched and cyclic, saturated and unsaturated hydrocarbon-based radicals containing from 1 to 6 carbon atoms, which are optionally substituted with at least one halogen;

X is a radical chosen from —OH, —OR$_4$, —NH$_2$, —NHR$_4$, —NR$_4$R$_5$, —SR$_4$, —COOR$_4$ and —COR$_4$;
wherein R$_4$ and R$_5$, which may be identical or different, are each chosen from linear, branched and cyclic, saturated and unsaturated hydrocarbon-based radicals containing from 1 to 6 carbon atoms, optionally substituted with 1 to 5 groups, which may be identical or different, chosen from —OH; —OR; —O—COR; —SH; —SR; —S—COR; —NH$_2$; —NHR; —NRR'; —NH—COR; -Hal (halogen); —CN; —COOR; and —COR;
wherein R and R', which may be identical or different, are each chosen from linear, branched and cyclic, saturated and unsaturated hydrocarbon-based radicals containing from 1 to 6 carbon atoms, which are optionally substituted with at least one halogen, R and R' optionally forming, together with N in the —NRR', a 5- or 6-membered carbon-based ring which may further comprise at least one hetero atom chosen from O, N and S in the ring, and/or which may be substituted with 1 to 5 groups, which may be identical or different, chosen from —OH; —OR"; —O—COR"; —SH; —SR";
—S—COR"; —NH$_2$; —NHR"; —NH—COR"; -Hal (halogen); —CN; —COOR"; and —COR"; wherein R" is chosen from linear, branched and cyclic, saturated and unsaturated hydrocarbon-based radicals containing from 1 to 6 carbon atoms, which are optionally substituted with at least one halogen;
R$_4$ and R$_5$ optionally forming, together with N in the —NR$_4$R$_5$, a 5- or 6-membered carbon-based ring which may further comprise at least one hetero atom chosen from O, N and S in the ring, and/or which may be substituted with 1 to 5 groups, which may be identical or different, chosen from —OH; —OR"; —O—COR"; —SH; —SR";
—S—COR"; —NH$_2$; —NHR"; —NH—COR"; -Hal (halogen); —CN; —COOR"; and —COR"; wherein R" is chosen from linear, branched and cyclic, saturated and unsaturated hydrocarbon-based radicals containing from 1 to 6 carbon atoms, which are optionally substituted with at least one halogen;
the mineral acid and organic acid salts thereof, and the optical isomers thereof, in isolated form and as a racemic mixture, with the exception of the following compounds:
N-acetylglycyl-N-(benzyl)-DL-valylglycine tert-butyl ester;
N-acetylglycyl-N-(2-nitrobenzyl)-DL-valylglycine tert-butyl ester; and
N-acetylglycyl-N-(2,4-dimethyloxybenzyl)-DL-valylglycine tert-butyl ester.

2. The process according to claim 1, wherein the skin is chosen from facial skin and body skin.

3. The process according to claim 1, wherein the skin is the scalp.

4. The process according to claim 1, wherein the at least one sign of ageing is generated by at least one of a reduction in the elasticity of the skin and a degradation of the collogen in the structure of the tissues.

5. The process according to claim 1, wherein
Y is oxygen, and/or
R$_1$ is chosen from (i) hydrogen;
(ii) linear and branched, saturated and unsaturated, hydrocarbon-based radical containing 1 to 12 carbon atoms, optionally substituted with at least one group chosen from —OH, —OR and —P(O)—(OR)$_2$ with R representing a linear, branched or cyclic, saturated or unsaturated hydrocarbon-based radical containing 1 to 6 carbon atoms, which is optionally substituted with at least one halogen; and/or $R_2$ is chosen from linear, branched and cyclic, saturated and unsaturated, hydrocarbon-based radical containing 1 to 12 carbon atoms optionally substituted with at least one group chosen from —OH and —OR with R representing a linear, branched or cyclic, saturated or unsaturated hydrocarbon-based radical containing 1 to 6 carbon atoms, which is optionally substituted with at least one halogen; and/or $R_3$ is a radical of formula $C_6H_{(5-y')}$—$B_{y'}$, in which y' is an integer ranging from 1 to 3, or a radical of formula -A-$C_6H_{(5-y)}$—$B_y$, in which y is an integer ranging from 0 to 2; and/or the radical A of $R_3$ is a linear or branched, saturated or unsaturated, divalent hydrocarbon-based radical containing 1 to 12 carbon atoms optionally substituted with at least one group chosen from halogen; —CN; —COOR; —NO$_2$;

SO$_2$—OR, with R representing a linear, branched or cyclic, saturated or unsaturated hydrocarbon-based radical containing 1 to 6 carbon atoms, which is optionally substituted by at least one halogen; and/or the radical B of $R_3$, which may be identical or different, is chosen from OR; —NHR; —CN; —COOR; —COR and linear and branched, saturated and unsaturated, hydrocarbon-based radical containing 1 to 12 carbon atoms optionally substituted with at least one group chosen from halogen; —CN; —COOR; —NO$_2$;

SO$_2$—OR, with R representing a linear, branched or cyclic, saturated or unsaturated hydrocarbon-based radical containing 1 to 6 carbon atoms, which is optionally substituted by at least one halogen; and/or X is a radical chosen from —OH and OR$_4$ with R$_4$ representing a linear, cyclic or branched, saturated or unsaturated hydrocarbon-based radical containing 1 to 6 carbon atoms, which is optionally substituted by at least one group chosen from —OH and OR with R representing a linear, branched or cyclic, saturated or unsaturated hydrocarbon-based radical containing 1 to 6 carbon atoms, which is optionally substituted by at least one halogen.

6. The process according to claim 1, wherein
$R_1$ is chosen from methyl, ethyl, propyl and isopropyl radical, each of which is optionally substituted with at least one group chosen from OH and —P(O)—(OR)$_2$ with R representing methyl, ethyl, propyl or isopropyl; and/or $R_2$ is chosen from methyl, ethyl, propyl, isopropyl, n-butyl, tert-butyl and isobutyl radical; and/or $R_3$ is chosen from one of the following formulae:

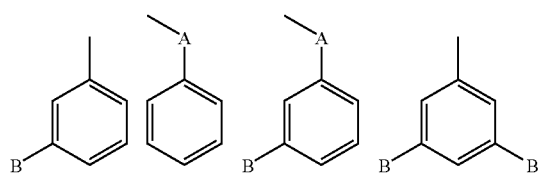

in which the divalent radical A is a methylene, an ethylene or a propylene and/or the radical B, which may be identical or different, represents —OR; —NHR; —CN; —COOR; —COR in which R represents a methyl, ethyl, propyl or isopropyl, or B represents a methyl, ethyl, propyl or isopropyl each of which is optionally substituted with at least one halogen, and/or X represents a radical chosen from —OH, OCH$_3$, —OC$_2$H$_5$, —O—C$_3$H$_7$ and —OC$_4$H$_9$.

7. The process according to claim 6, wherein B represents CF$_3$.

8. The process according to claim 1, wherein
$R_1$ is methyl, optionally substituted with a group P(O)—(OR)$_2$ with R representing ethyl; and/or
$R_2$ is isopropyl radial; and/or
$R_3$ represents a group chosen from one of the following formulae:

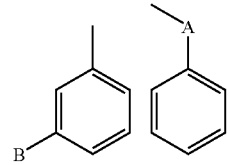

in which the divalent radical A is methylene, and/or the radical B represents CF$_3$, and/or
X represents a radical chosen from —OH and —OC$_2$H$_5$.

9. The process according to claim 1, wherein the at least one compound of formula (I) is chosen from
{2-[acetyl(3-trifluoromethylphenyl)amino]-3-methylbutyrylamino}acetic acid,
ethyl {2-[acetyl(3-trifluoromethylphenyl)amino]-3-methylbutyrylamino}acetate,
[2-(acetylbenzylamino)-3-methylbutyrylamino]acetic acid,
ethyl [2-(acetylbenzylamino)-3-methylbutyrylamino]acetate, and
ethyl (2-{benzyl[(diethoxyphosphoryl)acetyl]amino}-3-methylbutyrylamino)-acetate.

10. The process according to claim 8, wherein the at least one compound of formula (I) is {2-[acetyl(3-trifluoromethylphenyl)amino]-3-methylbutyrylamino}acetic acid.

11. The process according to claim 1, wherein the skin that has at least one sign of ageing is chosen from skin with wrinkles, skin with fine lines, wizened skin, skin lacking elasticity, skin lacking tone, skin suffering from a thinned dermis, skin suffering from degradation of collagen fibres, flaccid skin, thinned skin, and skin suffering from internal degradation following exposure to ultraviolet radiation.

12. A process for at least one of inhibiting the activity of elastases, limiting degradation of elastic fibres, and combating degradation of elastic fibres, comprising applying to the skin at least one composition, comprising, in a physiologically acceptable medium, at least one compound chosen from compounds of formula (I):

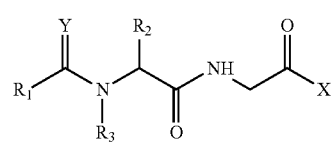

(I)

wherein:
Y is chosen from O and S,
R₁ is chosen from:
(i) hydrogen;
(ii) linear, branched and cyclic, saturated and unsaturated hydrocarbon-based radicals containing from 1 to 18 carbon atoms,
optionally substituted with 1 to 5 groups, which may be identical or different, chosen from —OH; —OR; —O—COR; —SH; —SR; —S—COR; —NH₂; —NHR; —NRR'; —NH—COR; -Hal (halogen); —CN; —COOR; —COR; —P(O)—(OR)₂; and —SO₂—OR;
wherein R and R', which may be identical or different, are each chosen from linear, branched and cyclic, saturated and unsaturated hydrocarbon-based radicals containing from 1 to 6 carbon atoms, which are optionally substituted with at least one halogen, the said radicals R and R' optionally forming, together with N in the —NRR', a 5- or 6-membered carbon-based ring which may further comprise at least one hetero atom chosen from O, N and S in the ring, and/or which may be substituted with 1 to 5 groups, which may be identical or different, chosen from —OH; —OR"; —O—COR"; —SH; —SR"; —S—COR"; —NH₂; —NHR"; —NH—COR"; -Hal (halogen); —CN; —COOR"; and —COR"; wherein R" is chosen from linear, branched and cyclic, saturated and unsaturated hydrocarbon-based radicals containing from 1 to 6 carbon atoms, which are optionally substituted with at least one halogen; and
(iii) radicals chosen from —OR; —NH₂; —NHR; —NRR'; —NH—COR; —COOR; and —COR;
wherein R and R', which may be identical or different, are each chosen from linear, branched and cyclic, saturated and unsaturated hydrocarbon-based radicals containing from 1 to 6 carbon atoms, which are optionally substituted with at least one halogen, the said radicals R and R' optionally forming, together with N in the —NRR', a 5- or 6-membered carbon-based ring which may further comprise at least one hetero atom chosen from O, N and S in the ring, and/or which may be substituted with 1 to 5 groups, which may be identical or different, chosen from —OH; —OR"; —O—COR"; —SH; —SR"; —S—COR"; —NH₂; —NHR"; —NH—COR"; -Hal (halogen); —CN; —COOR"; and —COR"; wherein R" is chosen from linear, branched and cyclic, saturated and unsaturated hydrocarbon-based radicals containing from 1 to 6 carbon atoms, which are optionally substituted with at least one halogen;
R₂ is chosen from linear, branched and cyclic, saturated and unsaturated hydrocarbon-based radicals containing from 1 to 18 carbon atoms, optionally substituted with 1 to 5 groups, which may be identical or different, chosen from —OH; —OR; —O—COR; —SH; —SR; —S—COR; —NH₂; —NHR; —NRR'; —NH—COR; -Hal (halogen); —CN; —COOR; and —COR;
wherein R and R', which may be identical or different, are each chosen from linear, branched and cyclic, saturated and unsaturated hydrocarbon-based radicals containing from 1 to 6 carbon atoms, which are optionally substituted with at least one halogen, R and R' optionally forming, together with N in the —NRR', a 5- or 6-membered carbon-based ring which may further comprise at least one hetero atom chosen from O, N and S in the ring, and/or which may be substituted with 1 to 5 groups, which may be identical or different, chosen from —OH; —OR"; —O—COR"; —SH; —SR"; —S—COR"; —NH₂; —NHR"; —NH—COR"; -Hal (halogen); —CN; —COOR"; and —COR"; wherein R" is chosen from linear, branched and cyclic, saturated and unsaturated hydrocarbon-based radicals containing from 1 to 6 carbon atoms, which are optionally substituted with at least one halogen;

R₃ is a radical chosen from those of formulae (II) and (III):

-A-C₆H₍₅₋ᵧ₎—Bᵧ  (II)

—C₆H₍₅₋ᵧ'₎—Bᵧ'  (III)

wherein:
y is an integer ranging from 0 to 5 and y' is an integer ranging from 1 to 5;
A is chosen from linear and branched, saturated and unsaturated divalent hydrocarbon-based radicals containing from 1 to 18 carbon atoms,
optionally substituted with 1 to 5 groups, which may be identical or different, chosen from —OH; —OR; —O—COR; —SH; —SR; —S—COR; —NH₂; —NHR; —NRR'; —NH—COR; -Hal (halogen); —CN; —COOR; —COR; —NO₂; and —SO₂—OR;
wherein R and R', which may be identical or different, are each chosen from linear, branched and cyclic, saturated and unsaturated hydrocarbon-based radicals containing from 1 to 6 carbon atoms, which are optionally substituted with at least one halogen, R and R' optionally forming, together with N in the —NRR', a 5- or 6-membered carbon-based ring which may further comprise at least one hetero atom chosen from O, N and S in the ring, and/or which may be substituted with 1 to 5 groups, which may be identical or different, chosen from —OH; —OR"; —O—COR"; —SH; —SR"; —S—COR"; —NH₂; —NHR"; —NH—COR"; -Hal (halogen); —CN; —COOR"; and —COR"; wherein R" is chosen from linear, branched and cyclic, saturated and unsaturated hydrocarbon-based radicals containing from 1 to 6 carbon atoms, which are optionally substituted with at least one halogen;
B, which may be identical or different, is chosen from —OH; —OR; —O—COR; —SH; —SR; —S—COR; —NH₂; —NHR; —NRR'; —NH—COR; -Hal (halogen); —CN; —COOR; —COR; —NO₂; and —SO₂—OR, and linear and branched, saturated and unsaturated hydrocarbon-based radicals containing from 1 to 18 carbon atoms,
optionally substituted with 1 to 5 groups, which may be identical or different, chosen from —OH; —OR; —O—COR; —SH; —SR; —S—COR; —NH₂; —NHR; —NRR'; —NH—COR; -Hal (halogen, or even perhalogen); —CN; —COOR; —COR; —NO₂; and —SO₂—OR;
wherein R and R', which may be identical or different, are each chosen from linear, branched and cyclic, saturated and unsaturated hydrocarbon-based radicals containing from 1 to 6 carbon atoms, which are optionally substituted with at least one halogen, R and R' optionally forming, together with N in the —NRR', a 5- or 6-membered carbon-based ring which may further comprise at least one hetero atom chosen from O, N and S in the ring, and/or which may be substituted with 1 to 5 groups, which may be identical or different, chosen from —OH; —OR"; —O—COR"; —SH; —SR"; —S—COR"; —NH₂; —NHR"; —NH—COR"; -Hal (halogen); —CN; —COOR"; and —COR"; wherein R" is chosen from linear, branched and cyclic, saturated and unsaturated hydrocarbon-based radicals containing from 1 to 6 carbon atoms, which are optionally substituted with at least one halogen;
X is a radical chosen from —OH, —OR₄, —NH₂, —NHR₄, —NR₄R₅, —SR₄, —COOR₄ and —COR₄;

wherein $R_4$ and $R_5$, which may be identical or different, are each chosen from linear, branched and cyclic, saturated and unsaturated hydrocarbon-based radicals containing from 1 to 6 carbon atoms, optionally substituted with 1 to 5 groups, which may be identical or different, chosen from —OH; —OR; —O—COR; —SH; —SR; —S—COR; —NH$_2$; —NHR; —NRR'; —NH—COR; -Hal (halogen); —CN; —COOR; and —COR;

wherein R and R', which may be identical or different, are each chosen from linear, branched and cyclic, saturated and unsaturated hydrocarbon-based radicals containing from 1 to 6 carbon atoms, which are optionally substituted with at least one halogen, R and R' optionally forming, together with N in the —NRR', a 5- or 6-membered carbon-based ring which may further comprise at least one hetero atom chosen from O, N and S in the ring, and/or which may be substituted with 1 to 5 groups, which may be identical or different, chosen from —OH; —OR''; —O—COR''; —SH; —SR'';
—S—COR''; —NH$_2$; —NHR''; —NH—COR''; -Hal (halogen); —CN; —COOR''; and —COR''; wherein R'' is chosen from linear, branched and cyclic, saturated and unsaturated hydrocarbon-based radicals containing from 1 to 6 carbon atoms, which are optionally substituted with at least one halogen;

$R_4$ and $R_5$ optionally forming, together with N in the —$NR_4R_5$, a 5- or 6-membered carbon-based ring which may further comprise at least one hetero atom chosen from O, N and S in the ring, and/or which may be substituted with 1 to 5 groups, which may be identical or different, chosen from —OH; —OR''; —O—COR''; —SH; —SR'';
—S—COR''; —NH$_2$; —NHR''; —NH—COR''; -Hal (halogen); —CN; —COOR''; and —COR''; wherein R'' is chosen from linear, branched and cyclic, saturated and unsaturated hydrocarbon-based radicals containing from 1 to 6 carbon atoms, which are optionally substituted with at least one halogen;

the mineral acid and organic acid salts thereof, and the optical isomers thereof, in isolated form and as a racemic mixture, with the exception of the following compounds:

N-acetylglycyl-N-(benzyl)-DL-valylglycine tert-butyl ester;

N-acetylglycyl-N-(2-nitrobenzyl)-DL-valylglycine tert-butyl ester; and

N-acetylglycyl-N-(2,4-dimethyloxybenzyl)-DL-valylglycine tert-butyl ester.

13. The process according to claim 12, wherein the skin is chosen from facial skin and body skin.

14. The process according to claim 12, wherein the skin is the scalp.

15. The process according to claim 12, wherein
Y is oxygen, and/or
$R_1$ is chosen from (i) hydrogen;
(ii) linear and branched, saturated and unsaturated, hydrocarbon-based radical containing 1 to 12 carbon atoms, optionally substituted with at least one group chosen from —OH, —OR and —P(O)—(OR)$_2$ with R representing a linear, branched or cyclic, saturated or unsaturated hydrocarbon-based radical containing 1 to 6 carbon atoms, which is optionally substituted with at least one halogen; and/or
$R_2$ is chosen from linear, branched and cyclic, saturated and unsaturated, hydrocarbon-based radical containing 1 to 12 carbon atoms optionally substituted with at least one group chosen from —OH and —OR with R representing a linear, branched or cyclic, saturated or unsaturated hydrocarbon-based radical containing 1 to 6 carbon atoms, which is optionally substituted with at least one halogen; and/or $R_3$ is a radical of formula $C_6H_{(5-y')}$—$B_{y'}$ in which y' is an integer ranging from 1 to 3, or a radical of formula -A-$C_6H_{(5-y)}$—$B_y$ in which y is an integer ranging from 0 to 2; and/or the radical A of $R_3$ is a linear or branched, saturated or unsaturated, divalent hydrocarbon-based radical containing 1 to 12 carbon atoms optionally substituted with at least one group chosen from halogen; —CN; —COOR; —NO$_2$;

SO$_2$—OR, with R representing a linear, branched or cyclic, saturated or unsaturated hydrocarbon-based radical containing 1 to 6 carbon atoms, which is optionally substituted by at least one halogen; and/or the radical B of $R_3$, which may be identical or different, is chosen from OR; —NHR; —CN; —COOR; —COR and linear and branched, saturated and unsaturated, hydrocarbon-based radical containing 1 to 12 carbon atoms optionally substituted with at least one group chosen from halogen; —CN; —COOR; —NO$_2$;

SO$_2$—OR, with R representing a linear, branched or cyclic, saturated or unsaturated hydrocarbon-based radical containing 1 to 6 carbon atoms, which is optionally susbstituted by at least one halogen; and/or X is a radical chosen from —OH and OR$_4$ with $R_4$ representing a linear, cyclic or branched, saturated or unsaturated hydrocarbon-based radical containing 1 to 6 carbon atoms, which is optionally substituted by at least one group chosen from —OH and OR with R representing a linear, branched or cyclic, saturated or unsaturated hydrocarbon-based radical containing 1 to 6 carbon atoms, which is optionally substituted by at least one halogen.

16. The process according to claim 12, wherein
$R_1$ is chosen from methyl, ethyl, propyl and isopropyl radical, each of which is optionally substituted with at least one group chosen from OH and —P(O)—(OR)$_2$ with R representing methyl, ethyl, propyl or isopropyl; and/or $R_2$ is chosen from methyl, ethyl, propyl, isopropyl, n-butyl, tert-butyl and isobutyl radical; and/or $R_3$ is chosen from one of the following formulae:

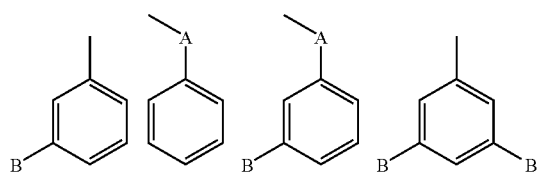

in which the divalent radical A is a methylene, an ethylene or a propylene and/or the radical B, which may be identical or different, represents —OR; —NHR; —CN; —COOR; —COR in which R represents a methyl, ethyl, propyl or isopropyl, or B represents a methyl, ethyl, propyl or isopropyl each of which is optionally substituted with at least one halogen, and/or X represents a radical chosen from —OH, OCH$_3$, —OC$_2$H$_5$, —O—C$_3$H$_7$ and —OC$_4$H$_9$.

17. The process according to claim 16, wherein B represents CF$_3$.

18. The process according to claim 12, wherein $R_1$ is methyl, optionally substituted with a group P(O)—(OR)$_2$ with R representing ethyl; and/or $R_2$ is isopropyl radial; and/or $R_3$ represents a group chosen from one of the following formulae:

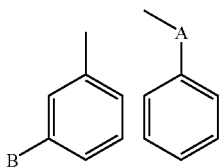

in which the divalent radical A is methylene, and/or the radical B represents CF$_3$, and/or X represents a radical chosen from —OH and —OC$_2$H$_5$.

19. The process according to claim 12, wherein the at least one compound of formula (I) is chosen from
- {2-[acetyl(3-trifluoromethylphenyl)amino]-3-methylbutyrylamino}acetic acid,
- ethyl {2-[acetyl(3-trifluoromethylphenyl)amino]-3-methylbutyrylamino}acetate,
- [2-(acetylbenzylamino)-3-methylbutyrylamino]acetic acid,
- ethyl [2-(acetylbenzylamino)-3-methylbutyrylamino]acetate, and
- ethyl (2-{benzyl[(diethoxyphosphoryl)acetyl]amino}-3-methylbutyrylamino)-acetate.

20. The process according to claim 19, wherein the at least one compound of formula (I) is {2-[acetyl(3-trifluoromethylphenyl)amino]-3-methylbutyrylamino}acetic acid.

21. A process for treating facial skin comprising, applying to the facial skin a composition comprising, in a cosmetically acceptable medium, 2-[acetyl(3-trifluoromethylphenyl)amino]-3-methylbutyrylamino}acetic acid.

* * * * *